(12) United States Patent
Nörtersheuser et al.

(10) Patent No.: US 6,489,289 B2
(45) Date of Patent: *Dec. 3, 2002

(54) METHOD FOR ESTABLISHING A DOSAGE PLAN FOR THROMBIN INHIBITORS

(75) Inventors: Peter Nörtersheuser, Mainz; Siegfried Kreis, Freinsheim, both of (DE)

(73) Assignee: Abbott Laboratories, Abbott Park, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/190,185

(22) Filed: Nov. 12, 1998

(65) Prior Publication Data

US 2001/0006620 A1 Jul. 5, 2001

(30) Foreign Application Priority Data

Dec. 15, 1997 (DE) .......................................... 19755682

(51) Int. Cl.⁷ ........................ A61K 38/00; A61K 35/14; A01N 43/04; C12Q 1/06
(52) U.S. Cl. ............................. 514/2; 514/12; 514/56; 530/324; 530/380; 530/381; 435/39
(58) Field of Search ................... 514/2, 12, 56; 530/324, 380, 381; 435/39

(56) References Cited

U.S. PATENT DOCUMENTS 4,745,177 A * 5/1988 Fritz et al. .................. 530/324

FOREIGN PATENT DOCUMENTS

WO    WO 93/16390    * 8/1993
WO    WO 94/29336    * 12/1994

OTHER PUBLICATIONS

Nowak et al., *Seminars in Thrombosis and Hemostasis*, vol. 22, No. 2, pp. 197–202, 1996.*
Delgado et al., *Critical Reviews in Therapeutic Drug Carrier Systems*, vol. 9, Nos. 3,4, pp. 249–304, 1992.*

* cited by examiner

*Primary Examiner*—Christopher S. F. Low
*Assistant Examiner*—Abdel A. Mohamed
(74) *Attorney, Agent, or Firm*—Keil & Weinkauf

(57) ABSTRACT

After a standard dose of a hirudin or an oral thrombin inhibitor is given to a recipient, the concentration of the hirudin or oral thrombin inhibitor in the blood of the recipient is determined using the ecarin clogging time test. From the ratio of the dose given to the recipient to the measured ecarin clotting time, a dosage plan-i.e., the dosage of the hirudin or oral thrombin inhibitor to be given thereafter-is established. For this purpose a pharmacokinetics/pharmacodynamics model is employed using a statistics program. A further dose of the hirudin or oral thrombin inhibitor is then administered to the recipient in accordance with the established dosage plan.

8 Claims, 10 Drawing Sheets

METHOD FOR ESTABLISHING A DOSAGE PLAN FOR THROMBIN INHIBITORS

The invention relates to a method for establishing a dosage plan for hirudins and/or oral thrombin inhibitors.

Thrombin plays an essential part as proteolytic enzyme in the coagulation of blood. Thrombin inhibitors are therefore interesting active substances for the treatment of disorders such as thrombosis. Particularly well known thrombin inhibitors are heparins, but also hirudin and hirudin derivatives, and oral thrombin inhibitors, the efficacy of these thrombin inhibitors being essentially determined by the blood or plasma levels of these compounds.

WO 93/16390 describes a method for determining hirudin and synthetic thrombin inhibitors in blood, in which a prothrombin intermediate, a compound which cleaves prothrombin to meizothrombin, a salt thereof or a mixture of these compounds and, where appropriate, buffers and/or other conventional additives are added to the blood or the blood component, and the time which elapses from the addition to the start of coagulation is measured.

The compound preferably used for cleaving prothrombin to meizothrombin is the snake venom ecarin. This method is therefore called the ecarin clotting test ("ECT") hereinafter. In this case, the coagulation is initiated by ecarin, and the intermediates which are trapped by hirudin or other thrombin inhibitors (not by heparin) are formed. After a certain time, when the hirudin or the other thrombin inhibitors present in the blood are consumed, the blood sample coagulates. The amount of thrombin inhibitor in the blood can be determined from the time to coagulation by calibration plots. However, WO 93/16390 makes no statement about the question as to how the concentration of a thrombin inhibitor in the blood of a patient can be predicted and thus adjusted optimally.

Clin. Pharmacokinet. 1997 Feb. 32 (2), 145-172 describes pharmacokinetic optimization in the treatment of deep venous thromboses, especially on treatment with heparin, reference being made to the need for individual monitoring of the dosage and the difficulties associated with nonlinear pharmacokinetics.

Because of the great inter- and intraindividual variability of heparin or other anticoagulants (e.g. also PEG-hirudin), intensive monitoring and individualized therapy is necessary in order to optimize the individual benefit/risk ratio of the treatment. Problems on treatment with heparin are, for example:

inappropriate initial heparin dose, long laboratory analysis times which impede rapid adjustment of the heparin dose, incorrect dose adjustment.

It is an object of the present invention to provide a method with which it is possible to establish in a simple and rapid manner a dosage plan for hirudins and oral thrombin inhibitors which is optimal for the individual patient, so that the risk of overdosage with the danger of hemorrhage and of underdosage with the danger of thrombosis is distinctly reduced or is eliminated.

We have found that this object is achieved by a) after giving a standard dose of the hirudin or of the oral thrombin inhibitor, determining the concentration of the hirudin or the oral thrombin inhibitor in the blood of the recipient using the ecarin clotting time test, and b) establishing, from the ratio of the dose given in step a) to the measured ecarin clotting time, using a computer program, e.g. the statistics program package p-PHARM 1.4, SIMED, 1996, on the basis of a pharmacokinetic/pharmacodynamic model, the dosage of the hirudin or oral thrombin inhibitor to be given thereafter.

The novel method makes it possible in a surprisingly simple manner to develop optimal dosage plans individually for particular patients, it being possible to minimize the risk of underdosage (with the danger of inadequate thrombin inhibition) just as well as, in particular, the risk of overdosage (with the danger of hemorrhages).

The invention additionally relates to the use of hirudins or oral thrombin inhibitors for producing a drug for use in the prophylaxis and treatment of thromboembolic events in accordance with a treatment schedule which comprises the following steps:

a) giving a standard dose of the hirudin or of the oral thrombin inhibitor, b) determining the ecarin clotting time and c) giving a further dose of the hirudin or of the oral thrombin inhibitor which has been established by means of a computer program, e.g. a statistics program package p-PHARM 1.4, SIMED 1996, on the basis of a pharmacokinetic/pharmacodynamic model, from the ratio of the dose given in step a) to the ecarin clotting time determined in step b).

It has emerged that use of the ecarin time method (ECT) in conjunction with the corresponding patients' data in the novel method provides excellent information in particular on the probability of hemorrhages on treatment with hirudins and/or oral thrombin inhibitors.

The novel method has the following advantages, inter alia:

performance of model simulations as supporting measure in the planning of clinical studies and monitoring of patients, identification and quantification of any dependencies of the pharmacokinetics/pharmacodynamics (pk/pd) on individual influencing factors (e.g. age, sex, renal excretion capacity, concurrent medication) to explain the variability in the observed drug effect within clinical studies, reduction of the laboratory analyses required through consistent application of the possibilities of sparse data analysis methods, increasing the rate of clinical development, identification of risk factors and patients at risk.

The hirudins employed in the present method are preferably the natural hirudins, but also recombinant hirudins or hirudins covalently bonded to organic carriers, as described, for example, in EP 209 061, in U.S. Pat. No. 4,745,177, in EP 345 616, in EP 502 962 or in DE 38 05 540. Hirudin bonded to polyethylene glycol (EP 502 962 A) and recombinant hirudin as indicated in EP 345 616 are particularly preferably employed.

Oral thrombin inhibitors which can be used are low molecular weight organic compounds which have the necessary oral availability. Oral thrombin inhibitors of this type are described, for example, in WO 94/29336, EP 669 317, WO 95/23609, or WO 96/25426, which are incorporated herein by reference. The oral thrombin inhibitors which are particularly employed are those having as structural unit a phenyl or heterocyclic ring with an amidine group as substituent.

The ecarin clotting time is determined using the method described in WO 93/16390.

In conjunction with the data on the recipient, i.e. the patient to be treated, in particular the sex, the body weight, the age and the kidney function or the renal excretion capacity, it is possible to establish from the ratio of the initial standard dose given to the measured ecarin clotting time, which shows a high linear correlation with the blood plasma level reached by the thrombin inhibitor, by means of a population-based pharmacokinetic/pharmacodynamic (pk/pd) model, a dosage plan from which it is evident, in particular, what the probabilities of hemorrhage are as a function of further doses of the thrombin inhibitor, and the possible danger of thrombosis with an underdosage.

The novel method can be employed irrespective of the use form, i.e. the thrombin inhibitors can be administered as infusion or i.v. bolus or as subcutaneous injection or else orally. Combined use forms are also possible, and even preferred for certain indications, e.g. unstable angina pectoris or peripheral arterial occlusive disease.

The dosage plan is established in the novel method as follows: Based on investigations of the pharmacokinetics and pharmacodynamics of PEG-hirudin (on the basis of data from more than 300 people), a mathematical model (FIG. 1) which is suitable for predicting and for simulating the time course of the PEG-hirudin concentration in the plasma and of the ecarin clotting time with various routes of administration has been developed. It allows an a priori dose recommendation to be given for example on the basis of demographic data for the patient (essentially age, sex, weight, smoker/non-smoker, kidney function).

However, it is regarded as even more essential for PEG-hirudin and the corresponding thrombin inhibitor to give reliable prognoses about the individual sensitivity and the subsequent concentration course on the basis of an early inhibitor concentration or ecarin clotting time determination. It is possible with this early measurement to forecast steady state concentrations and undertake any necessary dose corrections at an early stage.

Figure 1:
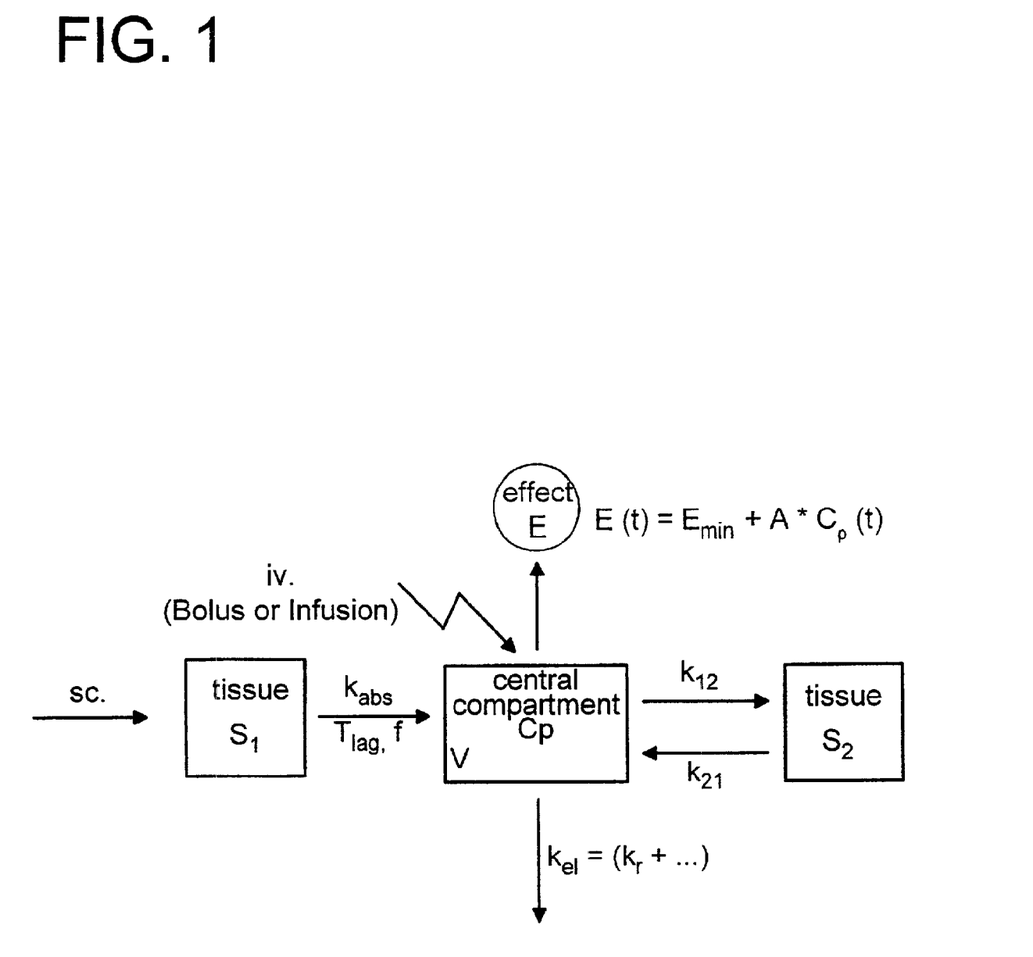

The abbreviations in FIG. 1 have the following meanings:

V: apparent volume of distribution [1]

$k_{el}$: apparent elimination rate [1/h], combines all the processes which contribute to the disappearance of PEG-hirudin from the system (e.g. metabolism, renal excretion of PEG-hirudin ($k_r$))

$Cl_{tot}$: total plasma clearance [1/h], calculated using $k_{el} * V$ $k_{12}$, $k_{21}$: transfer rates [1/h]

$k_{abs}$: absorption rate [1/h]

$T_{lag}$: time lag for absorption [h]

f: bioavailability on subcutaneous administration [dimensionless]

$E_{min}$: observed ecarin clotting time without PEG-hirudin acting (s)

A:, proportionality factor [ml * s/ng]

E(t): ecarin clotting time at time t (s)

Cp(t): PEG-hirudin concentration in the central compartment at time t [ng/ml]

$S_1$: PEG-hirudin concentration at the site of subcutaneous injection [ng/ml]

$S_2$: PEG hirudin concentration in the peripheral compartment [ng/1]

iv.: intravenous administration sc.: subcutaneous administration

The model functions for forecasting the time course of the inhibitor concentration and ecarin agglomeration time for a particular patient, indicated by the index i, can be represented as follows:

$$\frac{dS_1\_i}{dt} = -k_{abs\_i} \cdot S_{1\_i} \tag{1}$$

$$\frac{dCp\_i}{dt} = k_{abs\_i} \cdot S_{1\_i} - \left[\frac{Cl\_i}{v\_i} + k_{12\_i}\right] \cdot Cp\_i + k_{21\_i} \cdot S_{2\_i} \tag{2}$$

$$\frac{dS_2\_i}{dt} = -k_{12\_i} \cdot Cp\_i - k_{21\_i} \cdot S_{2\_i} \tag{3}$$

$E(t)=E_{min}+A \cdot Cp(t)$ $$E\_i(t)=E_{min\_i}+A\_i \cdot Cp\_i(t) \tag{4}$$

Based on the measured values of the model parameters it is possible to calculate approximately the following secondary variables, on the basis of which any necessary dose correction is eventually undertaken $C_{ss\_i}$: individual steady state inhibitor plasma concentration (ng/ml)

$$C_{ss\_i} = \frac{R°\_i}{v\_i \cdot k_{el\_i}} : \text{(infusion)} \tag{5}$$

$$C_{ss\_i} = \frac{D\_i \cdot f\_i}{v\_i \cdot k_{el\_i} \cdot \tau\_i} : \text{(subcutaneous injection)} \tag{6}$$

$E_{ss\_i}$: individual steady state ecarin agglomeration time (s)

$$E_{ss\_i}=E_{min\_i}+A \cdot C_{ss\_i} \tag{7}$$

where

D: dose administered in the dosage interval [mg]

R°: infusion rate [mg/h]

τ: dosage interval [h]

The interindividual variability relating to exposure to the inhibitor (e.g. PEG-hirudin) and to the ecarin time course is described mathematically by the individual grading of the model parameters (called fixed effects). This entails assuming a log normal distribution for those model parameters which prompt assumption of a distribution skewed to the right ($k_{abs}$, $k_{12}$, $k_{21}$). The logarithms of these model parameters show a normal distribution with the mean and with the variance-covariance matrix C (SIMED, 1996, P-PHARM, A Population Pharmacokinetic-Dynamic data Modeling Program, Version 1.4. SIMED, 94008 Creteil France). A normal distribution is assumed for the other model parameters (V, Cl, $E_{min}$, f).

A further assumption is that the inexplicable inter- and intraindividual effects (random effects) increase in proportion with the observed measurement (heteroskedastic measurement error).

The statistical analysis is carried out as follows:

Determination of the population and individual bayesian pk/pd parameters was carried out using the statistics program package P-PHARM 1.4 (SIMED, 1996), based on the EM algorithm, first described by Dempster et al. (Dempster, A. P., N. M. Laird, and D. B. Rubin, 1977. Maximum likelihood from incomplete data via the EM algorithm. Journal of the Royal Statistical Society, Series B, 39, 1–38). Mathematical details of the implemented algorithm are, dealt with in detail in the accompanying booklet from P-PHARM (SIMED, 1996), and by Bresolle et al. (Bresolle F., P. Ray, J. M. Jacquet, J. Bres et al., 1991. Cancer Chemother. Pharmacol., 29: 53–60), Fabre et al. (Fabre, D. Bresolle, F. R. Gomeni, O. Bouvet et al., 1993. Clin. Pharmacokinet., 24: 333–343) or Gomeni et al. (Gomeni R., G. Pineau, F. Mentre (1994). Population kinetics and conditional assessment of the optimal dosage regimen using the P-PHARM software package. Anticancer Res. 14: 2321-2326).

Further statistical analysis of the derived pk/pd parameters and identification of the covariables was carried out with the statistics program SAS (Version 6.12, Cary, N.C.: SAS Institute Inc., 1996).

Figure 2:
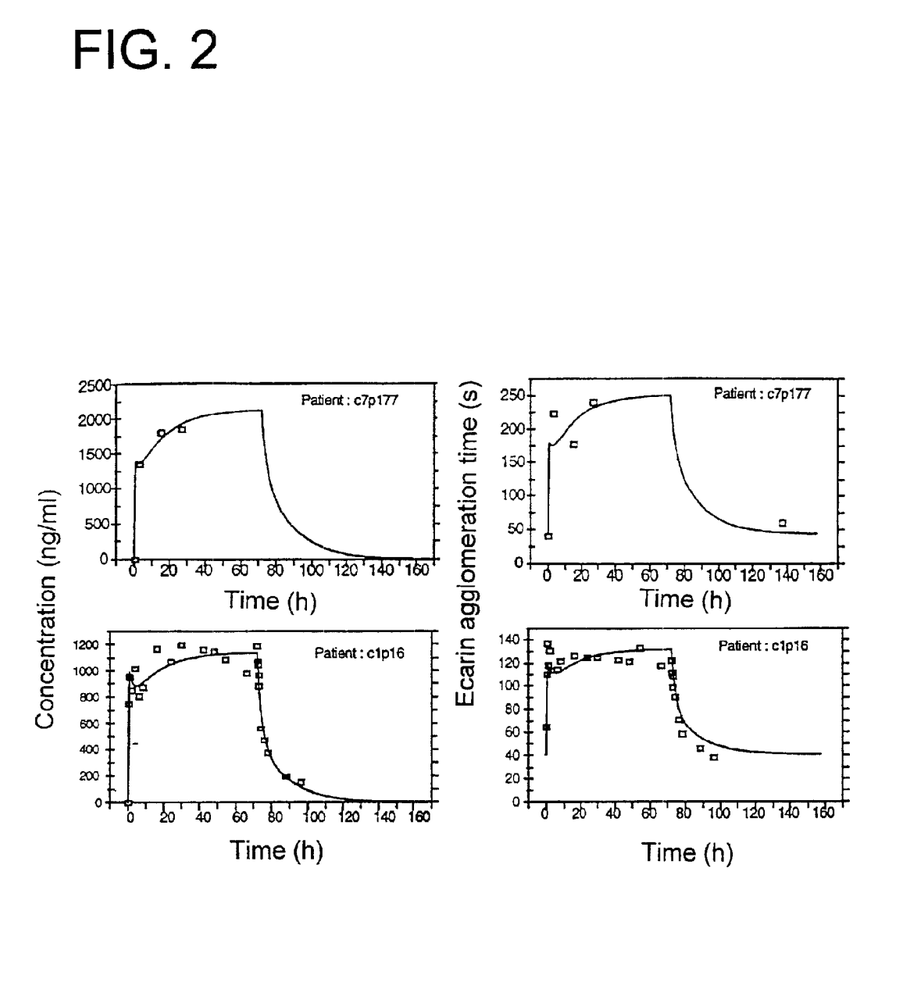

The population-based approach is particularly suitable when only a few measurements have been obtained for a large number of individuals. FIG. 2 represents the observed and estimated time course of the PEG-hirudin concentration in the plasma (left) and the ecarin agglomeration time (right) in two patients. If sufficient a priori knowledge of the pk/pd relationships is available from previous studies, quantification of the pk/pd course is possible even with a few observed values (above). Also evident from FIG. 2 is the good linear relation between PEG-hirudin concentration and ecarin clotting time. In such situations it is not possible to determine the individual pk/pd parameters using traditional methods of pk/pd analysis.

Based on the population-based pk/pd model for describing the behavior of PEG-hirudin after various types of administration and the collected experience from the previous studies it is possible, if necessary, to individualize the PEG-hirudin treatment. Such individualized therapy is based on comparison of the model behavior with the clinical behavior of the patient.

Figure 3:
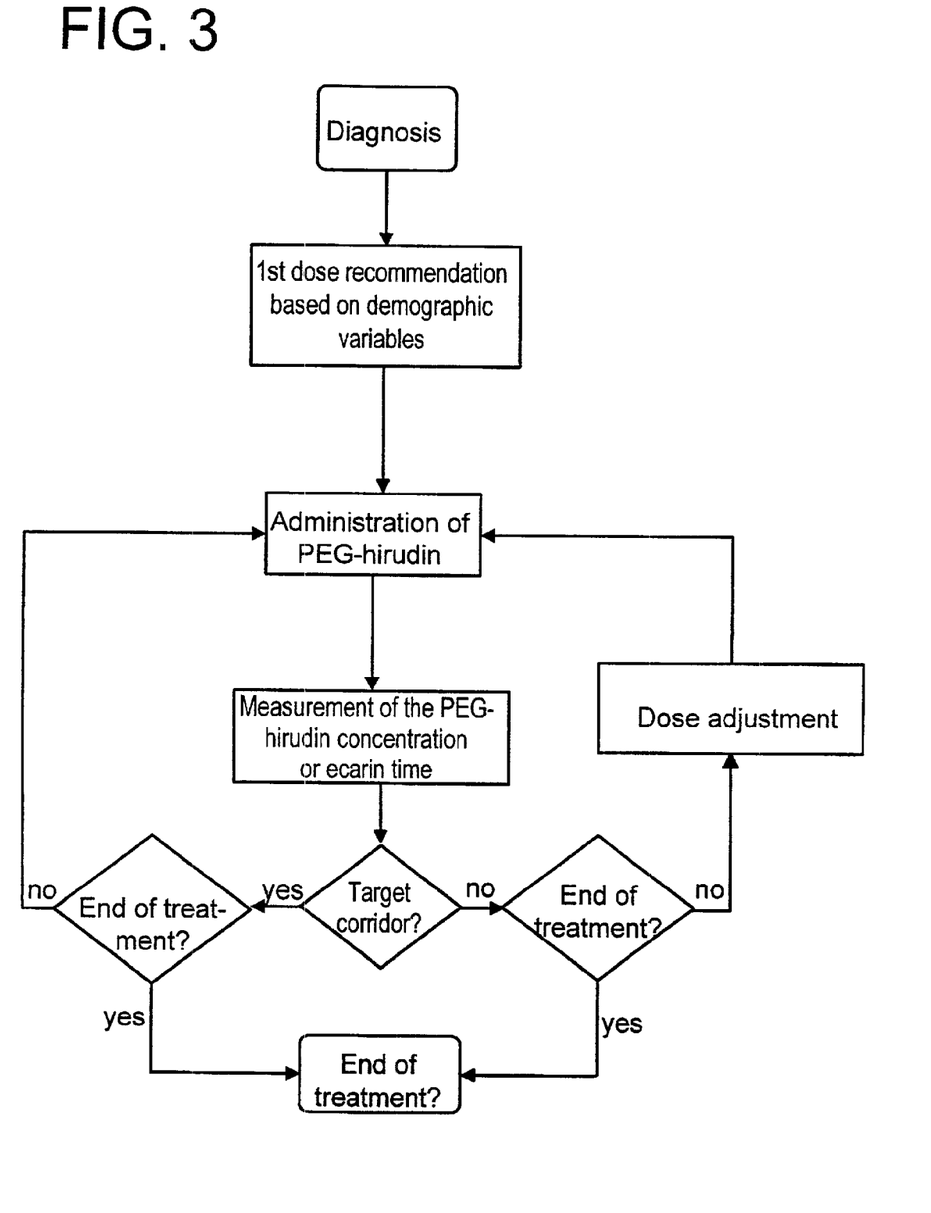

FIG. 3 shows a flow diagram for the treatment of patients with PEG-hirudin.

It has emerged from previous experience that an ecarin clotting time of more 250 s, preferably of more than 220 s, has no additional advantage for the patient so that this can be regarded as upper limit for any necessary dose adjustment. At the same time, the ecarin clotting time should not fall below 120 s, preferably 150 s, in the steady state.

These clinically obtained values are therefore used to specify a target corridor for the ecarin clotting time, which should be complied with. The novel method makes it possible very rapidly to determine for the individual patient which dosage must be chosen to comply with these upper and lower limits on further treatment, so that there is no risk related to hirudin for the group of patients.

EXAMPLE

Figure 4:
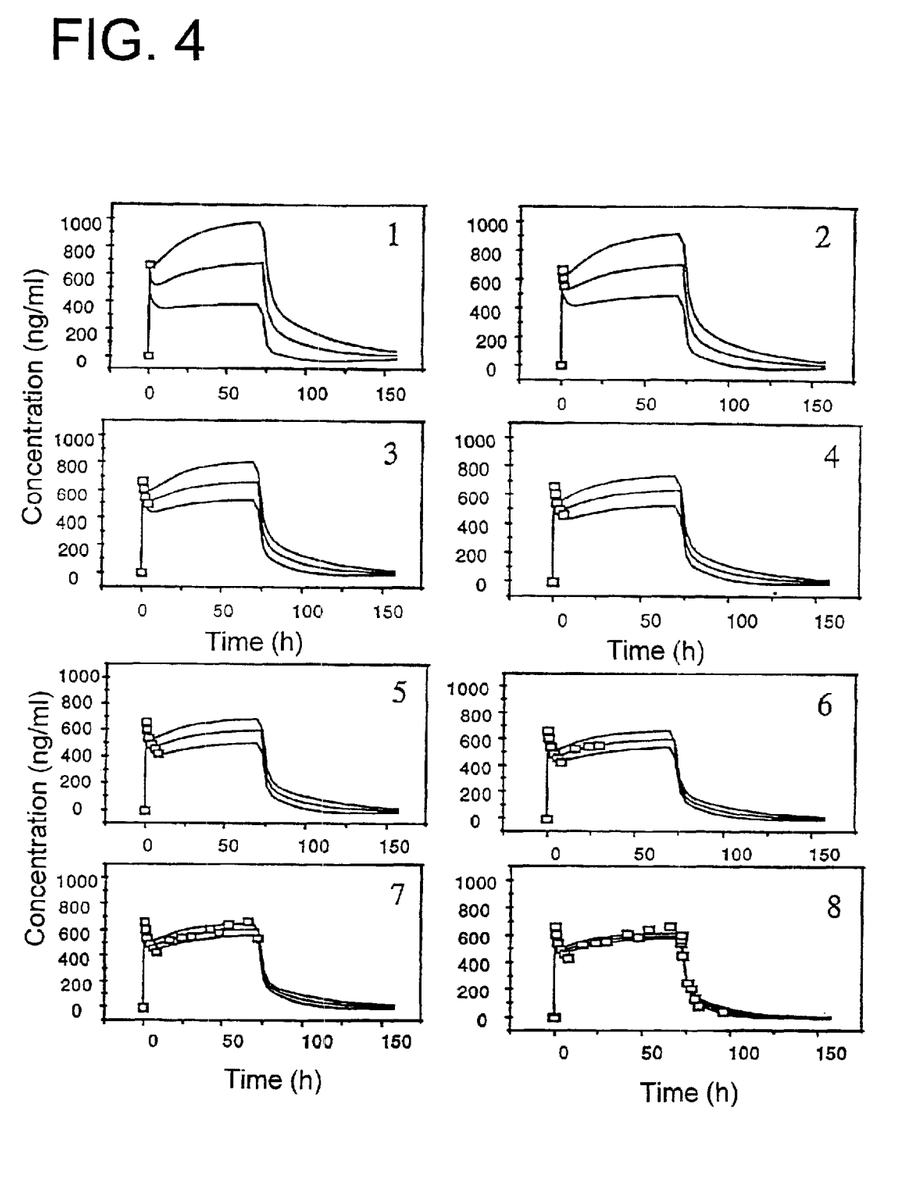

FIG. 4 shows in a series of graphs the dependence of the simulated course of the PEG-hirudin plasma concentration for a representative clinical patient on the number of measurement times included in the fitting to a model (mean course plus 95% tolerance interval). In the first simulation, only the first measurement, which took place half an hour after the start of the PEG-hirudin infusion, was included in the fitting to the model and, on this basis, the future course of the PEG-hirudin concentration in this patient was forecast. All the other measurements were neglected in this first simulation. In the subsequent fittings, increasing numbers of measurement times were included.

Figure 5:
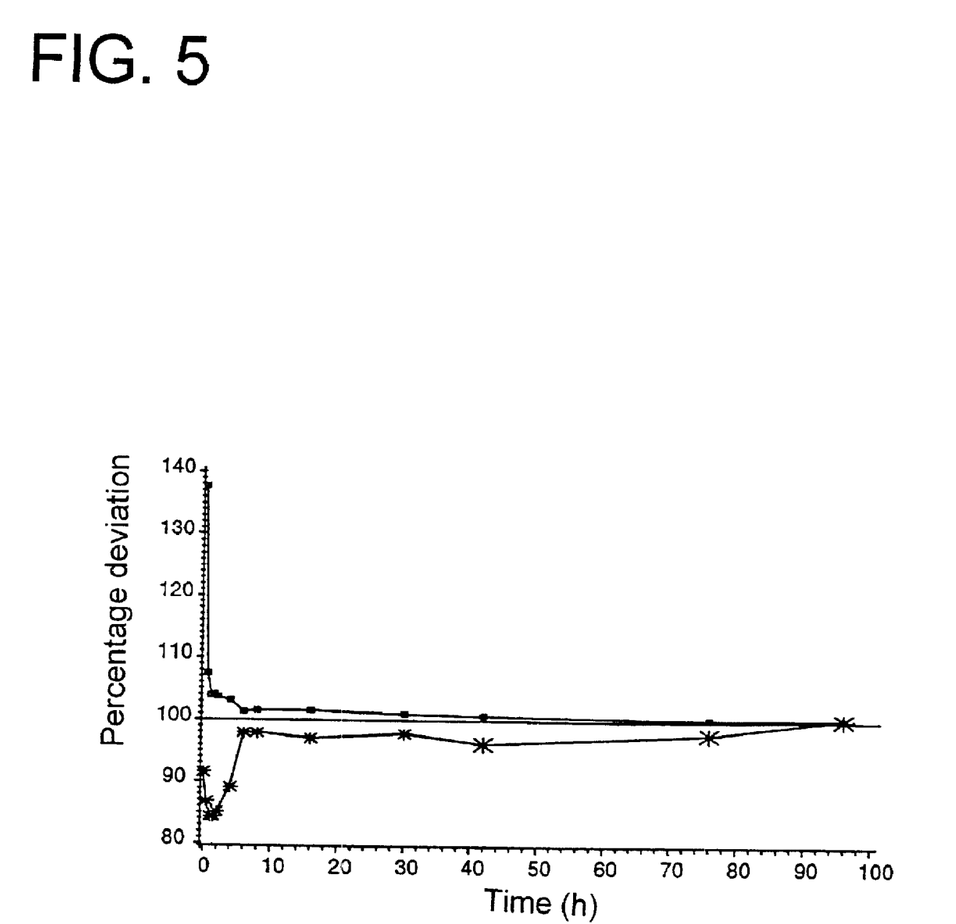

FIG. 5 shows the percentage deviation of the estimated values for the primary pharmacokinetic parameters 'apparent volume of distribution' (□) and 'clearance' (*) from the estimated values established including all the measurements for this patient. The estimated values for the volume of distribution and clearance are relatively constant after about 4 hours (about 5% of the total infusion time) so that it is possible even at an early time during the infusion to forecast with great certainty the steady state PEG-hirudin concentration in the plasma and, on this basis, to undertake any necessary dose correction.

This shows that a population-based pk/pd model approach together with a few early individual PEG-hirudin or ecarin agglomeration time measurements can be used as basis for any adaptation of the patients' doses in order to achieve therapeutic aims with PEG-hirudin more efficiently.

To validate the pk/pd model, the data observed for a group of 26 patients (=validation population) were excluded in the determination of the model parameters.

Figure 6:
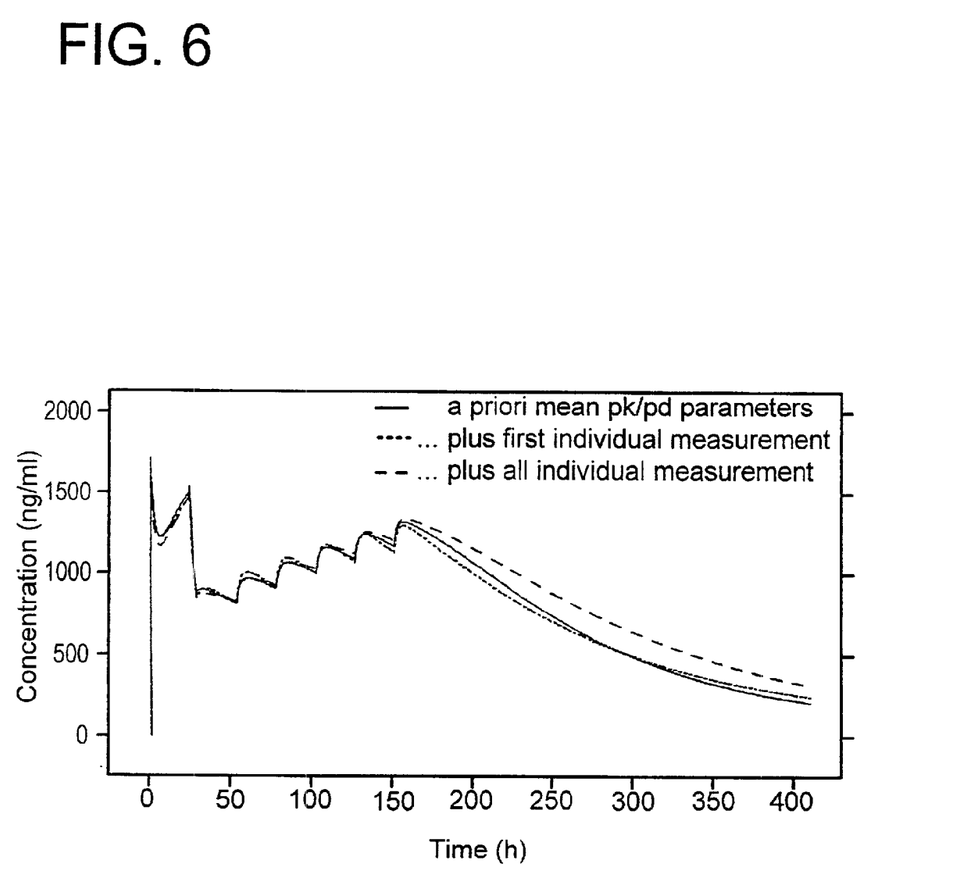

FIG. 6 shows the estimated mean course of the PEG-hirudin plasma concentration in these patients on the basis of the a priori values of the model parameters, i.e. with the estimated mean parameters calculated for the original population (full line). FIG. 6 also shows the estimated a posteriori concentration courses with inclusion of the first (dotted line), or all the individual PEG hirudin concentration measurements (broken line) on the validation population.

Figure 7:
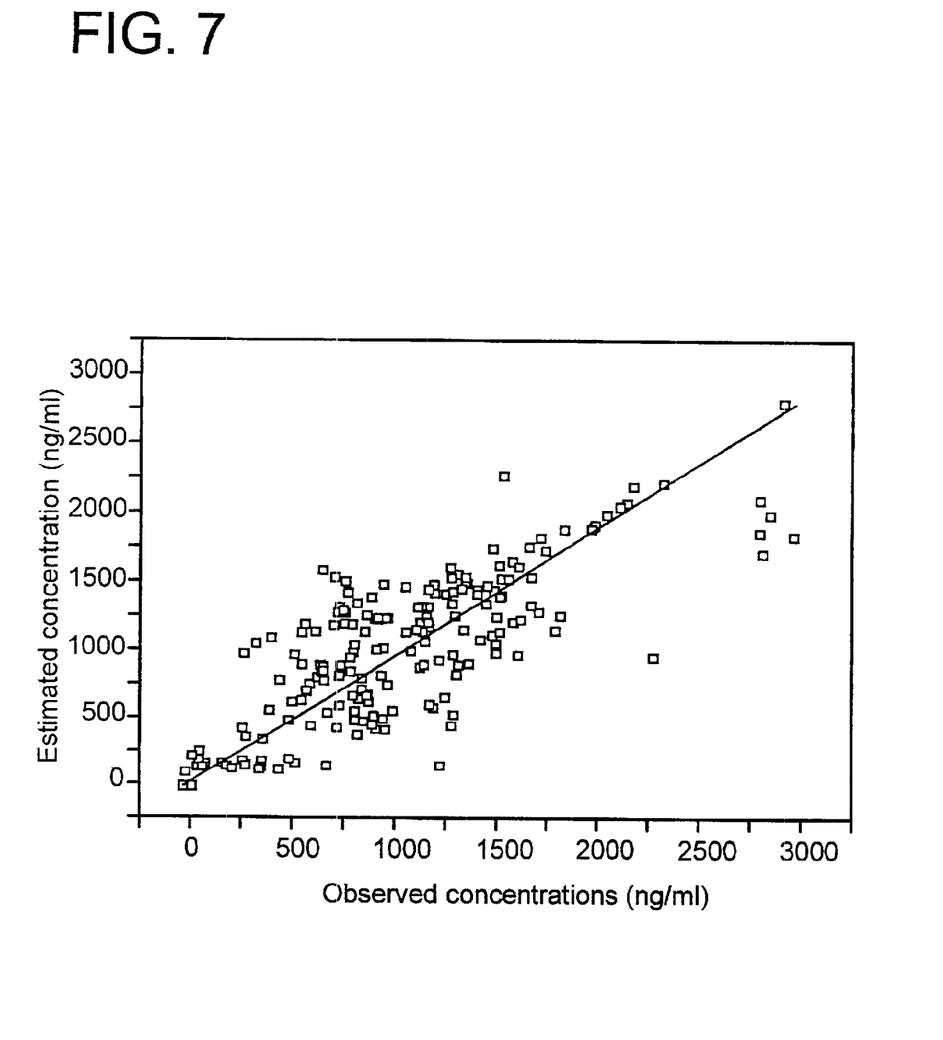

FIG. 7 compares the individual PEG-hirudin concentrations estimated a posteriori, with inclusion of the first individual measurement, with the observed values.

The agreement between the estimated concentration courses and the observed data is large, especially since a higher subcutaneous dosage was given to the validation population than to the original population and, of the demographic variables for the validation population, only the body weight was known at the time of the analysis. The individual deviations can thus be explained in part by the known, somewhat diminishing bioavailability with increasing subcutaneous dose.

Figure 8:
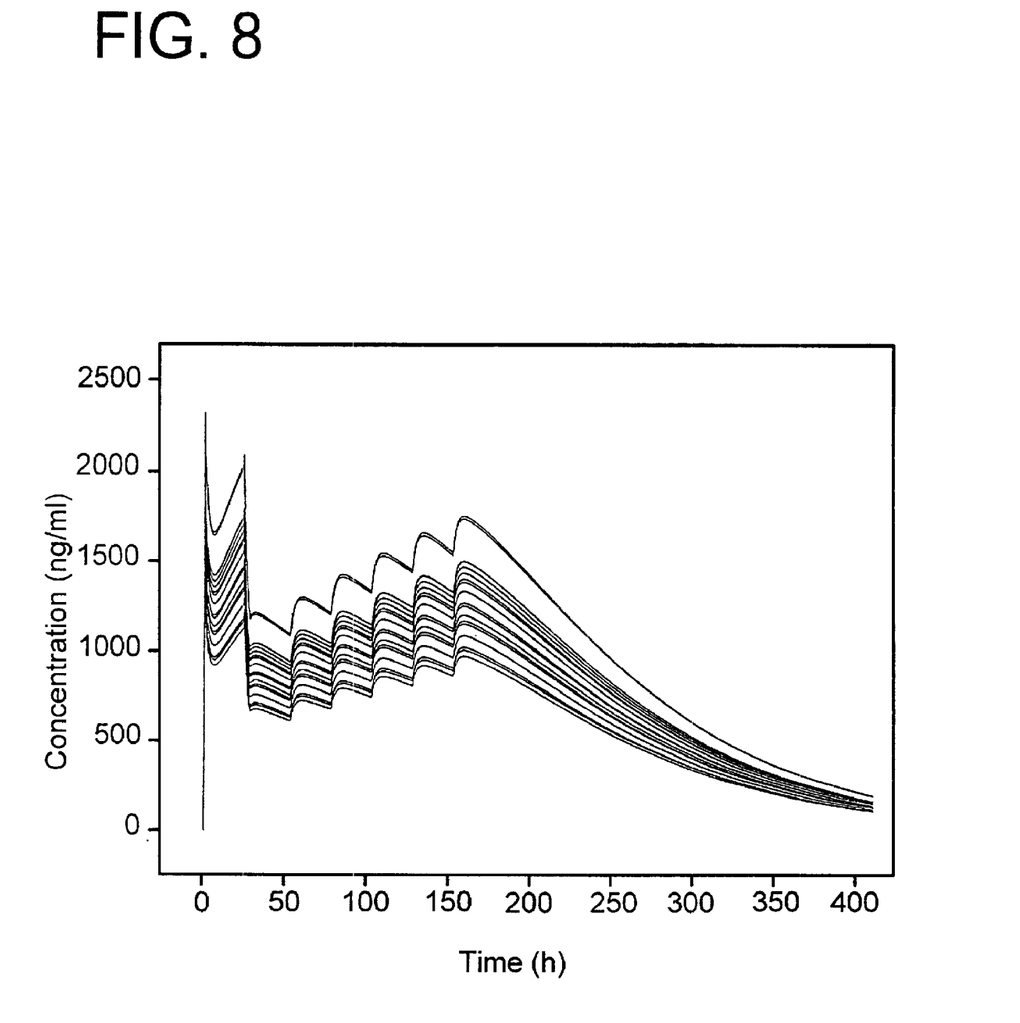
Figure 9:
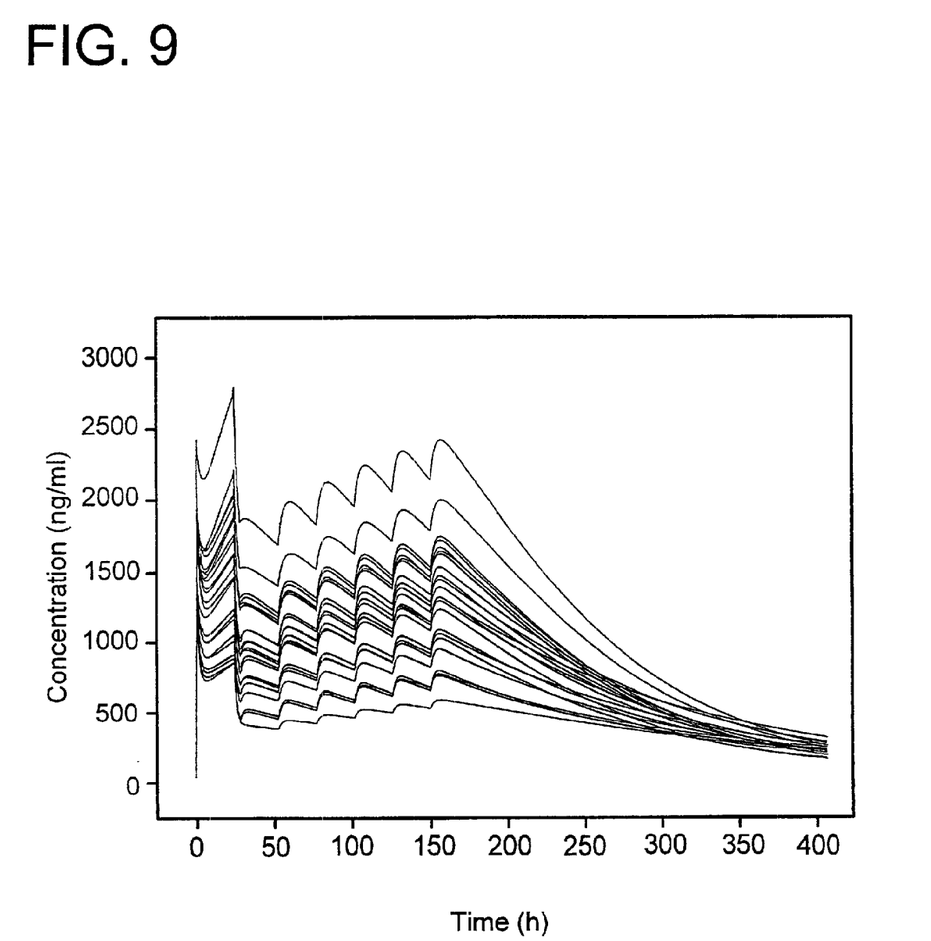
Figure 10:
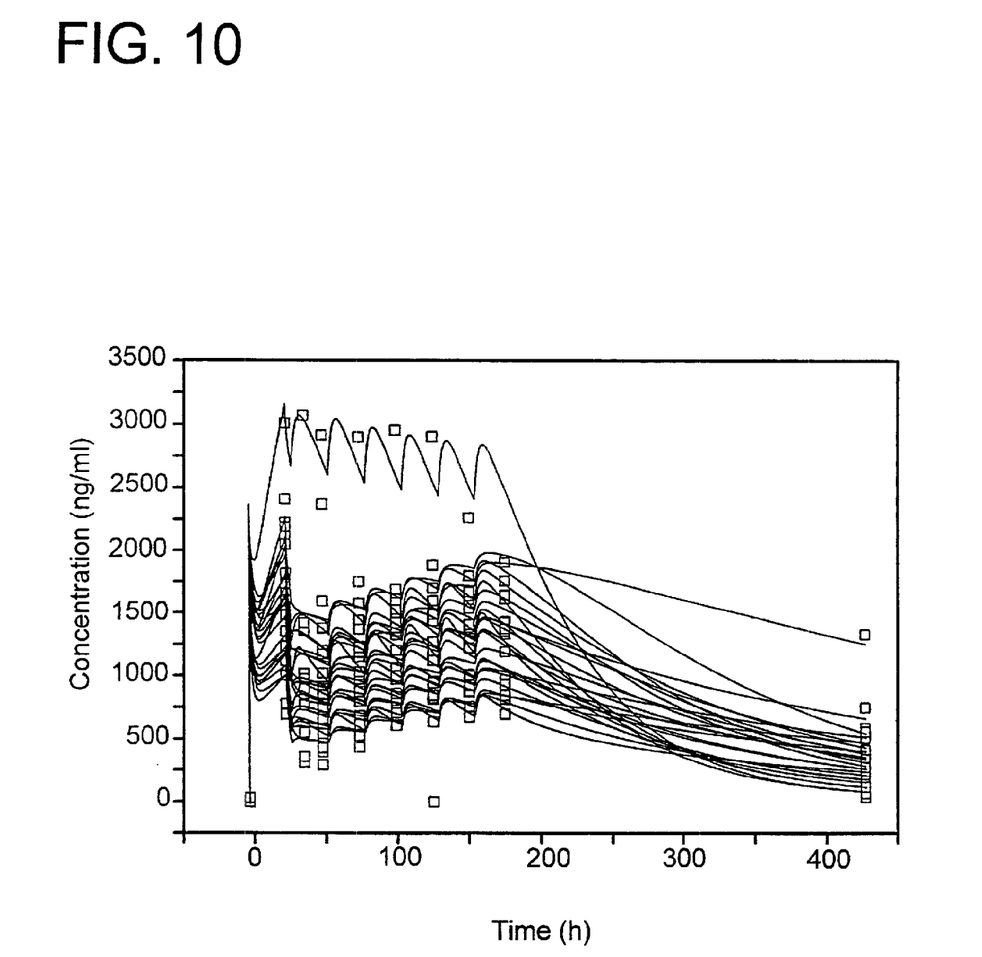

FIG. 8 shows the individual concentration courses estimated a priori for the validation population, and the individual concentration courses estimated a posteriori, with inclusion of the first, or all the individual concentration measurements (FIGS. 9 and 10).

The individual concentration courses estimated a priori (FIG. 8) show, apart from one patient, very good agreement with the observed courses. However, this patient could have been identified as patient at risk even after the first individual measurement (FIG. 9), and could have been observed correspondingly more intensively, or a dose adjustment could have been undertaken.

In summary, it can be stated that the utilizability of the pk/pd model described here for forecasting the individual behavior of PEG-hirudin is verified, and the pk/pd model can provide valuable assistance in monitoring PEG-hirudin.

We claim:

1. A method of establishing an a priori dosage for hirudin or an oral thrombin inhibitor in a patient based on demographic data and ecarin clotting time which method ccomprises the steps of a) administering a standard dose (SD) of the hirudin or oral thrombin inhibitor to the patient;

b) measuring the ecarin clotting time (ECT) to determine the concentration of the hirudin or oral thrombin inhibitor in the blood of the human; and c) determining the dosage plan of the hirudin or oral thrombin inhibitor from the SD to ECT ratio using a known statistics program on the basis of a pharmacokinetics and pharmacodynamics model represented by formula (6)

$$C_{ss\_}i = \frac{D\_i \times f\_i}{V\_i \times k_{el\_}i \times \tau\_i} \quad (6)$$

wherein $C_{ss\_}i$ is the patient's steady state inhibitor plasma concentration (ng/ml);

$D\_i$ is the dose administered to the patient within a dosage interval (mg);

$f\_i$ is the bioavailability of the hirudin on subcutaneous administration;

$k_{el\_}i$ is the elimination rate of the hirudin in the patient (l/h);

$V\_i$ is the apparent volume of distribution of hirudin in the patient (1); and $\tau\_$ is the dosage interval (h).

2. The method of claim 1 wherein the oral thrombin inhibitor is a compound having a phenyl or heterocyclic ring with an amide group as substituent.

3. The method of claim 1, wherein the hirudin is a natural hirudin, a recombinant hirudin or a synthetic hirudin which is covalently bonded to an organic carrier.

4. The method claim 3 wherein the organic carrier is polyethylene glycol.

5. A method for the prophylaxis or treatment of a thromboembolic event accordingly to a treatment schedule, which method comprises the steps of:

a) establishing an a priori dosage plan for hirudin or an oral thrombin inhibitor comprising:
1) administering a standard dose (SD) of the hirudin or oral thrombin inhibitor to a patient;
2) measuring ecarin clotting time (ECT) to determine the concentration of the hirudin or oral thrombin inhibitor in the blood of the patient; and
3) determining the dosage plan of the hirudin or oral thrombin inhibitor from the SD to ECT ratio using a statistics program on the basis of a pharmacokinetics and pharmacodynamics model represented by formula (6)

$$C_{ss\_}i = \frac{D\_i \times f\_i}{V\_i \times k_{el\_}i \times \tau\_i} \quad (6)$$

wherein $C_{ss}$-i is the patients steady state inhibitor plasma concentration (ng/ml);

$D$-$^i$ is the dose administered to the patient within a dosage interval (mg);

$f$-$^i$ is the bioavailability of the hirudin on subcutaneous administration;

$k_{el}$-$^i$ is the elimination rate of the hirudin in the patient (1/h);

$v$-$^i$ is the apparent volume of distribution of hirudin in the patient (1); and $T$-$^i$ is the dosage interval (h); and b) administering a further dose of the hirudin or oral thrombin inhibitor to the patient based on the established dosage plan.

6. The method of claim 5, wherein the oral thrombin inhibitor is a compound having a phenyl or heterocyclic ring with an amide group as substituent.

7. The method of claim 5, wherein the hirudin is a natural hirudin, a recombinant hirudin or a synthetic hirudin which is covalently bonded to an organic carrier.

8. The method of claim 7, wherein the organic carrier is polyethylene glycol.

* * * * *

UNITED STATES PATENT AND TRADEMARK OFFICE
CERTIFICATE OF CORRECTION

PATENT NO.    : 6,489,289 B2  
DATED         : December 3, 2002  
INVENTOR(S)   : Peter Nortersheuser et al.

It is certified that error appears in the above-identified patent and that said Letters Patent is hereby corrected as shown below:

<u>Title page,</u>
Item [30], should read as follows:

-- Dec. 15, 1997     (DE)..........19755682.5 --

Signed and Sealed this

Second Day of September, 2003

JAMES E. ROGAN
*Director of the United States Patent and Trademark Office*